United States Patent [19]

Moore et al.

[11] 4,015,196
[45] Mar. 29, 1977

[54] ANALYSIS OF MATERIALS
[75] Inventors: William Stanley Moore, Nottingham, England; Waldo Stephen Hinshaw, Pittsburgh, Pa.
[73] Assignee: National Research Development Corporation, London, England
[22] Filed: Apr. 3, 1975
[21] Appl. No.: 564,833
[30] Foreign Application Priority Data
Apr. 5, 1974 United Kingdom ............ 15280/74
Oct. 7, 1974 United Kingdom ............ 43365/74
[52] U.S. Cl. .............................. 324/.5 R; 324/.5 A
[51] Int. Cl.² ....................................... G01R 33/08
[58] Field of Search ............ 324/.5 R, .5 MA, .5 H, 324/.5 A

[56] References Cited
UNITED STATES PATENTS 3,530,371 9/1970 Nelson et al. ..................... 324/.5 R
3,789,832 2/1974 Damadian ........................ 324/.5 R
3,932,805 1/1976 Abe .................................. 324/.5 A Primary Examiner—R. V. Rolinec
Assistant Examiner—Michael J. Tokar
Attorney, Agent, or Firm—Cushman, Darby & Cushman

[57] ABSTRACT

A method of analyzing and apparatus for analyzing materials comprising subjecting a sample of the material to a non-homogeneous magnetic field having a predetermined time-dependency with respect to the sample such that a localized volume of the sample is subjected to a field the time dependent variation of which is unique with respect to the remainder of the sample. The sample is irradiated with radio-frequency energy to cause gyromagnetic resonance in the sample, and electrical energy produced by gyromagnetic resonance in the localized volume is measured.

7 Claims, 7 Drawing Figures

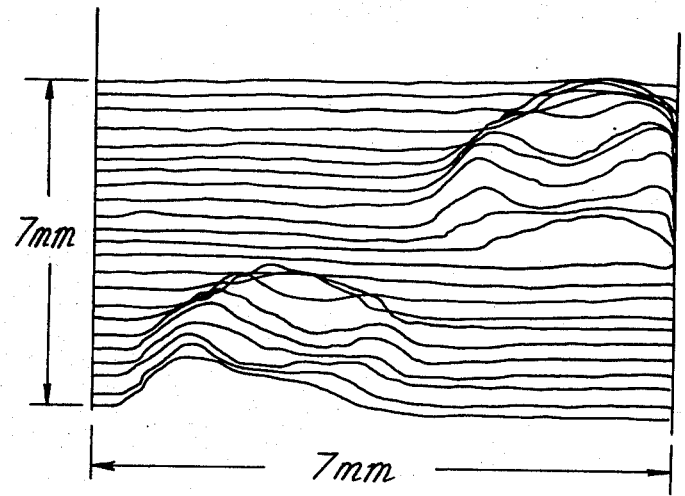
Fig. 5
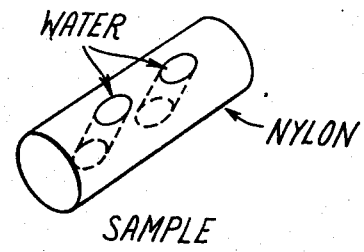

ANALYSIS OF MATERIALS

The present invention concerns the analysis of materials by gyromagnetic resonance techniques such as nuclear magnetic resonance and electron spin resonance and is particularly though not exclusively concerned with nuclear magnetic resonance spectroscopy.

In N.M.R. spectroscopy a sample to be analysed is subjected to an intense magnetic field and to radio frequency energy from a suitable source. This causes nuclear magnetic resonance in the sample which is picked up by coils in a receiver probe for subsequent analysis.

N.M.R. spectrometers have previously been limited to measurements of average properties of the sample. That is, if the sample were not uniform and homogeneous, the spectrometer could not distinguish the properties of one part of the sample from another.

It would naturally be a great advantage if it should also prove possible to obtain 3-dimensional plots or two dimensional maps of selected planes showing particular nuclear features such as nuclear spin density, nuclear spin relaxation time, molecular motion or flow with a three-dimensional object.

It has already been proposed to use static magnetic gradients surrounding the sample to give projections of the spin density along a line in the direction of the gradient. By taking a number of such projections it is possible to reconstruct mathematically a two-dimensional section through the plane of a three-dimensional object. However, the calculations required are lengthy and tedious.

In accordance with one aspect of the present invention, there is provided a method of investigating a sample comprising subjecting the sample to a non-homogeneous magnetic field having a predetermined time-dependency with respect to the sample such that a localised volume of the sample is subjected to a field the time dependent variation of which is unique with respect to the remainder of the sample, causing gyromagnetic resonance in the sample, and deriving an electrical signal from the energy produced by gyromagnetic resonance in said localised volume.

According to another aspect of the invention there is provided apparatus for use in analysing materials comprising means for generating a non-homogeneous magnetic field in which a sample to be analysed can be located, means for causing said non-homogeneous magnetic field to vary in a time-dependent manner so that a localised volume of said sample is subjected to a field the time dependent variation of which is unique with respect to the remainder of said sample, means for irradiating said sample with radio frequency energy, and means for deriving an electrical signal in response to gyromagnetic resonance occurring in said localised volume of said sample.

As is made clear in the remainder of the specification, the dimensions of the localised volume can take a number of different forms and in an idealised situation could be a point, a line or a plane. However, these idealised conditions are impossible to realise and, for example, the case of a plane would in practice approximate to a thin slice.

In the embodiment to be described a sample of a material to be analysed is subjected to a non-homogeneous time dependent magnetic field in a N.M.R. spectrometer. The result of this is that when the sample is irradiated with radio frequency energy to cause resonance in the sample, each part of the sample which is subjected to a field the time dependency of which is unique with respect to the remainder of the sample will give rise to a signal which is distinguishable from the signal produced from the rest of the sample.

The simplest arrangement is one in which the localised volume is constituted by a region in which the magnetic field strength is substantially invariant with time, as this region will give an output signal which is not affected by the time dependency of the inhomogeneous field.

Thus by filtering out all portions of the total output signal which contain this time dependency the remainder of the signal will relate to the region or localised volume where the magnetic field strength is invariant.

The size and nature of the localised volume will naturally depend on the method used to provide the time dependent inhomogeneous field. In the embodiment of FIG. 1 it is assumed that the localised volume approximates to a point determined by three independently variable field gradients each generated by appropriate coils.

However, it is to be appreciated that the localised volume could alternatively be a line or an area in accordance with the nature of the coils producing the effective field gradients.

Again, although the embodiment to be described is specifically concerned with the region of invariant field strength as being the localised volume from which information is extracted, it is entirely possible to select another localised volume provided that the magnetic field at the localised volume has a time dependence which is unique for that volume.

An embodiment of the present invention will now be described by way of example and with reference to the accompanying drawings in which;

FIG. 5 shows results obtained from a N.M.R. spectrometer of the kind to be described with reference to FIGS. 1 to 4.

Figure 1:
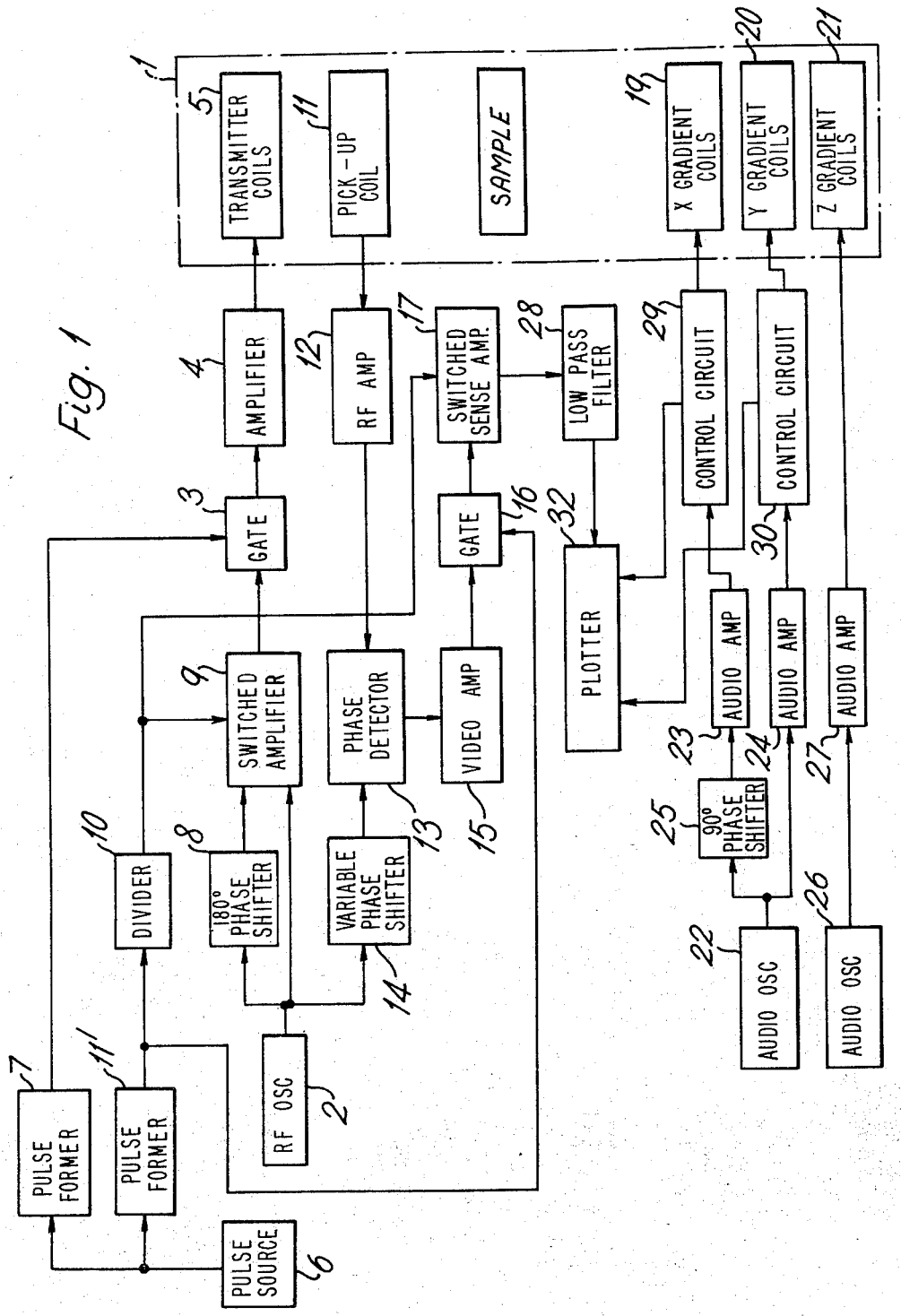
FIG. 1 is a circuit diagram of a N.M.R. spectrometer constructed in accordance with the present invention.

The N.M.R. spectrometer shown in FIG. 1 comprises a probe generally indicated at 1 within which can be mounted samples to be analysed. The probe 1 is disposed in an intense uniform magnetic field generated by a conventional magnet (not shown), the direction of this field being subsequently taken as the Z direction in a Cartesian co-ordinate system. As in a standard N.M.R. spectrometer, the sample is subjected to radio frequency energy from an r.f. oscillator 2 the output of which is gated by a gate 3 into pulses, amplified by an amplifier 4 and supplied to standard radio frequency transmitter coils 5 in the probe 1. The value of the radio frequency is chosen, having regard to the strength of the uniform magnetic field, so that a desired magnetic resonance will be excited in the sample. The gate 3 is controlled by a trigger pulse source 6 supplying a train of pulses at about 1 kilohertz to an r.f. gate pulse former 7 the output of which is taken to the gate 3.

In this embodiment the output of the r.f. oscillator 2 is divided into three parallel branches one of which contains a circuit 8 which shifts the phase of the oscillator output through 180°. This and another branch are taken to a switched input amplifier 9 the output of which is connected to the gate 3. The amplifier 9 is switched by pulses from a divide-by-two circuit 10 which halves the frequency of the pulses it receives from a video gate pulse former 11' in turn supplied with pulses by the trigger pulse source 6. Thus the amplifier 9 supplies signals to the gate 3 which alternate in phase by 180°. The changing of the phase of the r.f. pulses by 180° changes the sign of the signal from the sample.

The probe 1 also contains radio frequency pick-up coils 11 which pick up energy radiated as a result of nuclear magnetic resonance in the sample and this probe signal is amplified in a r.f. amplifier 12 and detected in a phase sensitive detector 13 controlled by a variable phase shift circuit 14 connected to the third output branch from the r.f. oscillator 2. The detected signal is amplified by a video amplifier 15, and is gated via a video gate 16 to a further switched sense amplifier 17. The purpose of the video gate 16 is to turn off the signal during those periods when a r.f. pulse is being supplied to the sample by the transmitter coils 5. The switched sense amplifier 17 switches the sign of the signal passing through it giving positive amplification after one pulse and negative amplification after the next and does so under the control of the divide-by-two circuit 10 which also controls the switched input amplifier 9.

Since as previously described the changing of the phase of the r.f. pulse by 180° changes the sign of the output signal from the sample, and since the amplifiers 9 and 17 are switched synchronously from the same source those portions of the final output from the amplifier 17 which are due to the signals picked up from the sample will always have the same sign. However, non-random noise which has been introduced into the signal will alternate in sign. Such noise can be caused by, for example, radio frequency leakage into the receiver from the oscillator 2 and other sources, by computer logic noise picked up by the receiver, by baseline off-set or by drift in the video amplifier.

Thus by averaging the signal in a signal averager this non-random noise can be removed. This would not be the case if signal averaging alone were employed as this would only be effective in improving the signal-to-noise ratio with respect to random noise.

The probe 1 also contains three pairs of coils 19, 20 and 21 for subjecting the sample to a non-homogeneous magnetic field which is superimposed on the uniform field generated by the magnet, this non-homogeneous field being made time dependent as described below. For the sake of clarity the coils 19, 20, 21 are shown in FIG. 1 at a distance from the sample, but their forms and disposition will be more fully explained in the following description with reference to FIGS. 2 and 3.

The sample is disposed in a cylindrical chamber (not shown) having a diameter of eight millimeters and a length of 40 millimeters, which is disposed with its axis parallel to the uniform magnetic field; this axis is taken as the Z-axis of the co-ordinate system. The coil pair 19 is disposed substantially in a plane perpendicular to the Z-axis, which is taken as the plane $Z=0$, the coils of this pair respectively comprising a pair of wires 40 and 41 extending on opposite sides of the Y-axis and each uniformly spaced by 7.5 millimeters from this axis. In operation currents are caused to flow through the wires 40 and 41 in the same direction, the remainder of the coils 19 being shaped so that the return paths for these currents are kept well away from the sample. The coil pair 19 thus generates a magnetic field which at points in the plane $Z=0$ between the wires 40 and 41 is directed parallel to the Z-axis and whose strength has a gradient in the X direction; the sign of this gradient is of course dependent on the sense of the currents flowing through the wires 40 and 41 and the field strength is zero at a particular value of the co-ordinate X determined by the relative magnitudes of these currents. The coil pair 20 is identical in form to and arranged in a similar manner to the coil pair 19, except that in this case the wires 40 and 41 extend parallel to the X-axis. The coil pair 21 is in the form of a Helmholtz pair wound in opposition and having a diameter of 25 millimeters, the coils of this pair being respectively disposed substantially in planes lying on opposite sides of the plane $Z=0$ and each uniformly spaced by 6.25 millimeters from this plane. In operation a current is caused to flow through the coils 21 so as to generate a magnetic field having a gradient in the Z direction and having zero strength in the plane $Z=0$, the sense of the gradient of course depending on the sense of the current flowing through the coils 21.

Figure 2A:
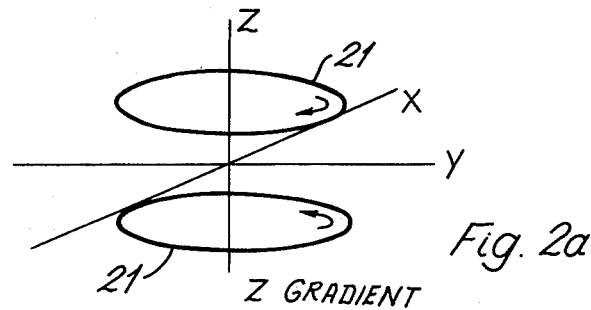
FIGS. 2a, 2b, 2c are perspective views of coils for providing an inhomogeneous magnetic field.
Figure 2B:
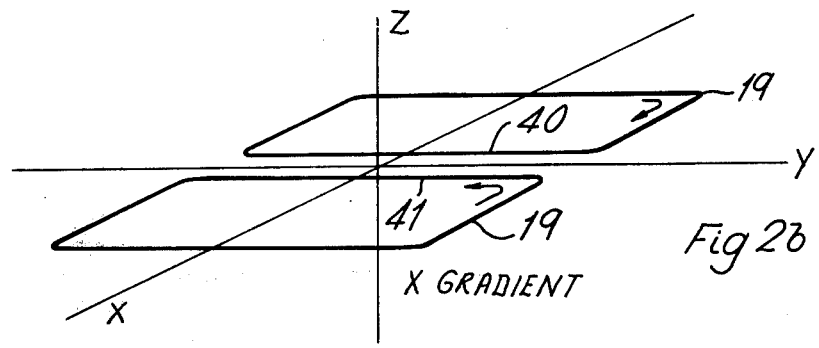
Figure 2C:
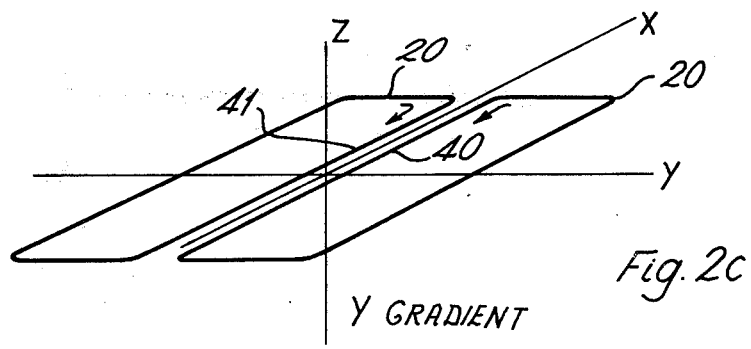
Figure 3:
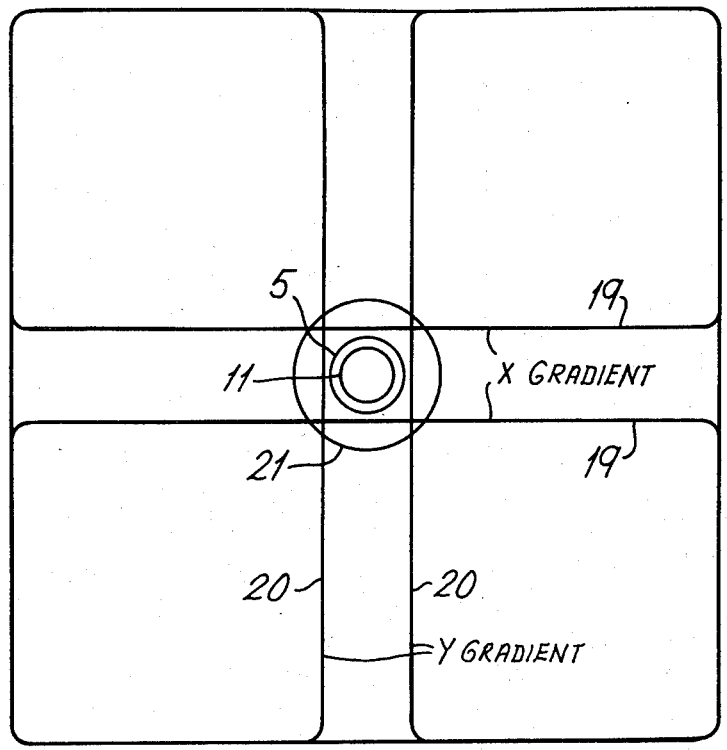
FIG. 3 is a plan view of the coils of the spectrometer of FIG. 1.

The layouts of the individual coil pairs 21, 19 and 20 are respectively illustrated in FIGS. 2a, 2b and 2c, while the overall arrangement is illustrated in FIG. 3, in which the positions of the transmitter coils 5 and pick-up coils 11 are also indicated. It will be appreciated that the overall magnetic field generated by the coils 19, 20 and 21 always has zero value in a localised volume approximating to a point in the plane $Z=0$, the position of this point in the plane being variable in the X direction by varying the ratio of the currents in the coils 19 and being variable in the Y direction by varying the ratio of the currents in the coils 20. The position of the plane $Z=0$ with respect to the sample can be varied by relative movement in the Z direction between the sample and the coils 19, 20 and 21.

The overall field generated by the coils 19, 20 and 21 is arranged to be time dependent in the following manner. Referring again to FIG. 1, there is provided an audio frequency oscillator 22 from which parallel outputs are taken to a pair of audio frequency amplifiers 23 and 24, the outputs of these amplifiers respectively being fed to the coil pairs 19 and 20 via control circuits 29 and 30 more fully described below. The signal fed to the amplifier 23 is phase shifted through 90° with respect to the signal fed to the amplifier 24, by means of a phase shift circuit 25. As a result the fields generated by the coils 19 and 20 combine to provide a rotating field gradient in the plane $Z=0$. There is also provided an audio frequency oscillator 26, whose output is fed to the coil pair 21 via an amplifier 27, so as to produce an alternating field gradient in the Z direction. For satisfactory operation, the frequencies of the oscillators 22 and 26 should be chosen so as to have non-integral relationships with the repetition frequency of the r.f. pulses.

As indicated above the overall magnetic field generated by the coils 19, 20 and 21 will always have zero value in a localised volume approximating to a point in the plane of the coils 19 and 20, so that the total magnetic field strength in this localised volume will be substantially invariant with time, being simply the strength of the field generated by the magnet. At all other points in the sample, however, the total magnetic field will have a complex time dependence. Thus by passing the output from the amplifier 17 through a suitable low pass filter 28 it is possible to remove from this output all components corresponding to N.M.R. signals generated at regions other than the revelent localised volume, so that only the component corresponding to N.M.R. signals from the localised volume is passed for subsequent processing. It will be appreciated that the filter 28 also performs the function of signal averaging referred to above.

Figure 4:
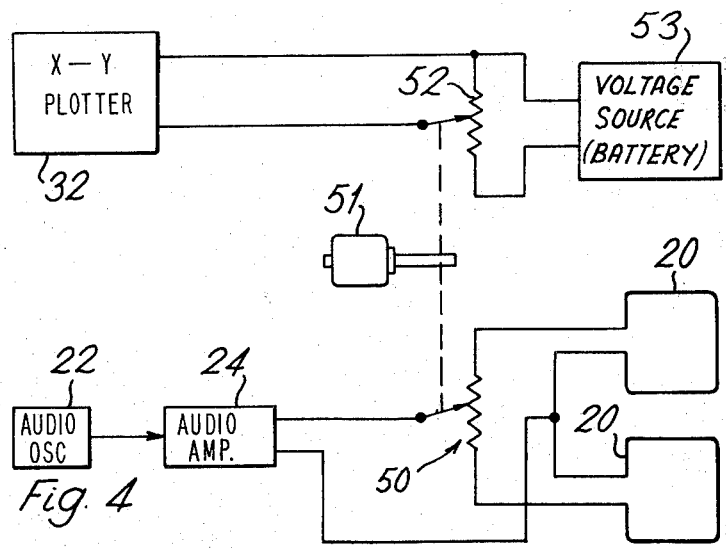
FIG. 4 is a circuit diagram of a circuit for controlling coils producing a magnetic gradient.

The control circuits 29 and 30, which are of identical form, are provided to enable the point in the plane Z=0 corresponding to the localised volume at which measurements are taken to be selected, the circuits 29 and 30 respectively determining the values of the X and Y co-ordinates of this point. The circuit 30 is shown in FIG. 4, and comprises a variable potentiometer 50 whose tapping point is driven by an electric motor 51 and across which the coils 20 are connected in series. The output of the amplifier 24 is connected between the tapping point of the potentiometer 50 and the junction between the coils 20. The control circuits 29 and 30 are respectively linked to the X and Y controls of an X-Y plotter 32 to which the output of the filter 28 is applied. Thus as shown in FIG. 4 the motor 51 also drives the tapping point of a variable potentiometer 52 which constitutes the Y control of the plotter 32, the potentiometer 52 being connected across a battery voltage source 53.

It will thus be seen that when the control circuits 29 and 30 are operated to vary the position of the "sensitive" point in the sample, the plotter 32 will provide a map of the N.M.R. signals derived from points in a section of the sample disposed perpendicular to the direction of the magnetic field generated by the magnet. This section may be selected by appropriate positioning of the sample relative to the coils 19, 20 and 21.

In alternative embodiments of the invention, different forms of display system could be used, for example incorporating an oscilloscope, or the output from the filter 28 could be fed to a computer. It is also envisaged that the selection of the mapped section of the sample could be effected by means of a control circuit, similar to the circuits 29 and 30, associated with the Z gradient coils, but in this case the form of the X and Y gradient coils would required some modification as compared with the form of the coils 19 and 20.

The specific configuration used for the coils 19 and 20 gives a high gradient strength for a given current and the coils can easily be made rigid since they are confined to a plane. The rigidity of the coils is necessary if high resolution is to be attained. The field produced by coils of this type is highly non-uniform, but only the value of the field in the plane of sensitivity is important and that plane is the plane of the coils. In this plane, the field produced is in the Z direction and can easily be calculated using the Biot and Savart law. Even in the plane, the gradient produced is far from uniform, but with the localised volume mapping technique described in this specification the uniformity of the gradient is unimportant. There are two aspects of the coil behaviour that are important in the present invention. One is the strength of the gradient at the point where the magnitude of the field is zero. The strength of the gradient at this point determines the size of the localised volume. The second is the location in the plane of sensitivity of the point of zero field. This coil configuration is such that both of these aspects can be calculated accurately. Thus the circuits driving the coils can be designed to keep the localised volume size constant and move the localised volume linearly. When this is done, there is a very little distortion in the final output.

The following considerations should be noted in respect of the employment of methods according to the invention in conjunction with pulsed N.M.R. spectrometry, in which the radio frequency pulses may be applied in a number of different modes.

Thus an r.f. pulse may be applied to the sample so as to cause resonance, the video gate opened after the application of the r.f. pulse, and a further r.f. pulse not applied until relaxation of the nuclei in the sample has occurred. It is essential that the video gate should be open long enough for several cycles of the time dependent magnetic field to have occurred.

However, the information rate, or information per unit time, for this method is poor. The reason for this is that the measurement cannot be repeated until the sample spin system has returned to thermal equilibrium.

However, if just after the video gate is opened and the signal detected, another r.f. pulse is applied which has an equal but opposite effect to the first, the effect of the two pulses largely cancels. Thus the experiment can be repeated much sooner than before since after the two pulses, the system is much closer to thermal equilibrium. This two pulse "pulse sequence" can be represented by $(a,+)t(a,-)T$ where $a$ is the width of the pulse, $+$ or $-$ is its sign or phase, $t$ is the time interval between the pulse pair, and T is the time interval before the sequence is repeated.

Further, this sequence can be modified so that the behaviour of the system between the pulses also tends to cancel. This is done by adding a third pulse, giving the sequence $(a,+)t(2a,-)t(a,+)T$. The centre pulse is twice the width of the other two pulses. This sequence has the additional advantage that the signal between the first and second pulses has the opposite sign from that between the second and third.

The time interval between sets of these three pulses, T, can be decreased to zero to give a high information rate. The sequence becomes a continuous string of phase alternated pulses, so that the sample produces an almost continuous signal proportional to the amplitude of its magnetisation. Thus this method provides high signal to noise per unit time. It will be appreciated that the embodiment of the invention illustrated in FIG. 1 can be regarded as operating either with the two pulse sequence referred to above (with T equal to $t$) or with the three pulse sequence referred to above (with T equal to zero).

Due to the cancelling effect of the alternating phase, the amplitude of the pulse is not critical. Thus inhomogeneties of the strength of the r.f. field throughout the sample are not critically important.

A further advantage is that it is necessary only to be near the resonance condition for this mode to work. The resonance condition for a particular nucleus is determined by the ratio of the strength of the resonant magnetic field and the frequency of the r.f. pulse. Thus small errors in either the strength of the field or the applied frequency will have little effect.

These advantages are combined with the synchronous noise reduction factor advantage already described in which by alternating the r.f. pulse phase after successive pulses many sources of noise such as baseline drift, can easily be removed in the final signal processing stages.

This sequence of alternate pulses also gives a measure of meagnetisation which is less affected by slow fluctuations in the field strength and r.f. frequency.

A continual monitor of the magnetisation of a sample is useful in various applications such as the following:

1. Since the magnetisation is proportional to the number of nuclei, monitoring the magnetisation allows a quick and continuous measure of the amount of a selected substance, for example, the amount of water in the sample. The insensitivity of this method to experimental conditions makes it particularly suitable for industrial applications such as measuring the amount of water in samples of coal.

2. Since the method continuously monitors the magnetisation of the sample, the direction of the magnetisation can be reversed by the application of a 180° r.f. pulse and its return to equilibrium directly observed. This measurement of recovery to equilibrium is much quicker than previous methods since the entire measurement is made in the time of one recovery. By maintaining the continuous monitoring pulses, the signal after the 180° pulse can be recorded in a digital signal averager and the experiment repeated to improve the signal to noise ratio.

Alternatively, the same information of the recovery to equilibrium may be obtained by applying, in addition to the continuous sampling pulses, 180° pulses spaced at regular intervals with the final time constant of the spectrometer much longer than the interval between the 180° pulses. Thus the output signal as the interval between the 180° pulses is swept gives the recovery of the magnetisation to equilibrium. This technique can be used to produce differential maps of magnetisation recovery rates.

3. The signal between the rapid phase alternated pulses is maintained as long as the changes in the resonance condition, etc., are not comparable to the pulse rate. If the integrated change between one pulse and the next is appreciable, the second pulse does not return the magnetisation to its previous position and the steady state condition is lost and the signal amplitude is reduced.

This destruction of the steady state condition provides a method of monitoring the magnetisation of some nuclei while that of others is ignored. As one example, if a time dependent magnetic field gradient is applied to a bulk sample, the magnetisation of the nuclei that experience a fluctuating field will not be observed. Thus the resulting signal arises only from those nuclei positioned such that the amplitude of the time dependent gradient field is zero. Thus measurements can be made in selected regions of the sample. Switching the sign of the time dependent gradient synchronously with the pulses can be used to ensure optimum effect.

4. Similar considerations allow self-diffusion, macroscopic flow, and other properties of the sample to be measured and continuously monitored with these techniques.

Although this specification has so far been concerned with locating the sample within a spectrometer, it is perfectly possible to generate magnetic fields in such a manner that once a sample has been subjected to a suitable fixed magnetic field, the time dependent field can be generated by a probe which does not surround the sample. Thus a sample to be examined might be placed in a static magnetic field between two poles and a handhold or otherwise controlled probe used to scan the sample. Alternatively the sample could be moved relative to fixed localised volume. Such arrangements would obviously have applications in the medical field.

As is shown in FIG. 5, which is the plot obtained from scanning a sample of Nylon containing two small volumes of water, it is possible to map the distribution of nuclei in a sample with a selected set of characteristics. It was possible to observe water protons and to ignore Nylon protons because of their differing $T_2$ relaxation times. Thus for example in animal samples the protons in muscle, fat, blood etc. have different relaxation times so that differential plots are possible that show up these various types of tissue. An important fact is that bone would be transparent to analysis of this kind and would not obscure the details as in x-rays. It has also recently been shown that protons in malignant tumours have different $T_1$ relaxation times from healthy tissue. Thus the techniques described would allow detailed study of a brain tumour without the need for an exploratory operation.

We claim:

1. A method of investigating a sample, the method comprising the steps of:
   causing gyromagnetic resonance to occur in said sample by irradiating said sample with radio frequency energy while subjecting said sample to a magnetic field, said field having a systematically varying non-homogeneous component such that said field is substantially invariant with time in a localized volume of said sample but varies with time in all other parts of said sample;
   receiving from said sample a signal resulting from said gyromagnetic resonance; and
   deriving from said signal information relating to gyromagnetic resonance effects specific to said localized volume, said information being distinguished by virtue of the difference between said localized volume and said other parts of said sample in respect of the time dependence of said field.

2. A method according to claim 1, in which said steps are performed a plurality of times in respect of said sample, the position of said localized volume in said sample being changed between successive performances of said steps.

3. A method according to claim 2, in which the changing of the position of said localized volume in said sample is effected at least partly by changing the form of said component of said field.

4. An apparatus for use in the investigation of samples by gyromagnetic resonance techniques, the apparatus comprising:
   means for generating a magnetic field in a region of space in which a sample to be investigated can be located, said generating means including modulating means for causing said field to have a systematically varying non-homogeneous component such that said field is substantially invariant with time in a localized volume of said region but varies with time in all other parts of said region;
   means for irradiating a sample located in said region with radio frequency energy to cause gyromagnetic resonance to occur in the sample when said generating means is operative;
   means for receiving from a sample located in said region a signal resulting from gyromagnetic resonance effects in the sample; and means for deriving from said signal information relating to gyromagnetic resonance effects specific to said localized volume, said information being distinguished by virtue of the difference between said localized volume and said other parts of said region in respect of the time dependence of said field.

5. An apparatus according to claim 4, in which said irradiating means comprises means for causing said radio frequency energy to be in the form of a train of pulses of an oscillation of given frequency, and said information deriving means comprises a phase-sensitive detector having an input and an output, means for controlling said detector by an oscillation of said given frequency, a first signal-translating channel connected between said receiving means and said input of said detector, a low pass filter, a second signal-translating channel connected between said output of said detector and said filter, and means for disabling said second signal-translating channel for the duration of each pulse of said train.

6. An apparatus according to claim 5, in which said irradiating means comprises means for causing successive pulses of said train to differ in phase by 180°, and said apparatus further comprises means for causing said second signal-translating channel to operate with opposite senses of signal translation during successive intervals between the pulses of said train.

7. An apparatus according to claim 4, in which said modulating means comprises means for changing the form of said component of said field so as to change the position of said localized volume in said region.

* * * * *